US00PP08793P

United States Patent [19]

Fischer

[11] Patent Number: Plant 8,793

[45] Date of Patent: Jun. 21, 1994

[54] HOLLY PLANT NAMED 'WYERIV'

[75] Inventor: Norman G. Fischer, Hillsboro, Md.

[73] Assignee: Wye Nursery, Inc., Hillsboro, Md.

[21] Appl. No.: 72,104

[22] Filed: Jun. 7, 1993

[51] Int. Cl.[5] ..... A01H 5/00
[52] U.S. Cl. ..... Plt./65
[58] Field of Search ..... Plt. 65

U.S. PATENT DOCUMENTS

PP 3,675 1/1975 Meserve ..... Plt./65

*Primary Examiner*—James R. Feyrer
*Attorney, Agent, or Firm*—Bruce M. Monroe; Costas S. Krikelis

[57] ABSTRACT

A new and distinct variety of female holly plant, having great merit as a landscape plant due to its attractive foliage, heavy production of large berries, and adaptability to a wide range of growing conditions, is herein described.

2 Drawing Sheets

FIELD OF THE INVENTION

This invention relates to a new and distinct variety of holly plant, having qualities and characteristics not exhibited by others. In particular, this invention relates to a new variety of female holly plant having great merit as a landscape plant due to its small dense foliage, its prolific production of berries, and its easy culture. The plant of this invention has been named, 'Wyeriv' for international name recognition purposes. It is expected that the plant of this invention will be marketed in this country under trademark 'River Queen'.

BACKGROUND

This new and distinct variety of Ilex, hereafter referred to Ilex ×. 'Wyeriv,' was selected from a group of seedlings in 1971. The plant is a superior specimen plant as a foundation plant or for landscape applications. Because of its highly attractive foliage and berries, cut branches can be used for interior decoration. It is a supposed hybrid of Ilex ×. Nellie R. Stevens and *Ilex cornuta*, but the male parentage is uncertain. The plant has been asexually propagated by cuttings at Wye Nursery in Caroline County on the Eastern Shore of Maryland.

BRIEF DESCRIPTION OF THE PHOTOGRAPHS

SUMMARY OF THE INVENTION

The invention is a new and distinct variety of Ilex produced solely by my efforts. The objective was a holly plant that is an improvement on the popular *Ilex cornuta* hybrids. Seedlings of Ilex ×. 'Nellie R. Stevens' were evaluated since this variety possesses many desirable characteristics. The selection, referred to as Ilex ×. 'Wyeriv,' produced an Ilex variety that is different not only from its parent but from any other Ilex known to me.

The male parent is unknown since the plant from which seeds were collected was growing in a nursery that contained many male species of Ilex. However, the shape and color of the foliage as well as the growth habit suggest a strong resemblance to some of the *Ilex cornuta* hybrids.

Figure 1:
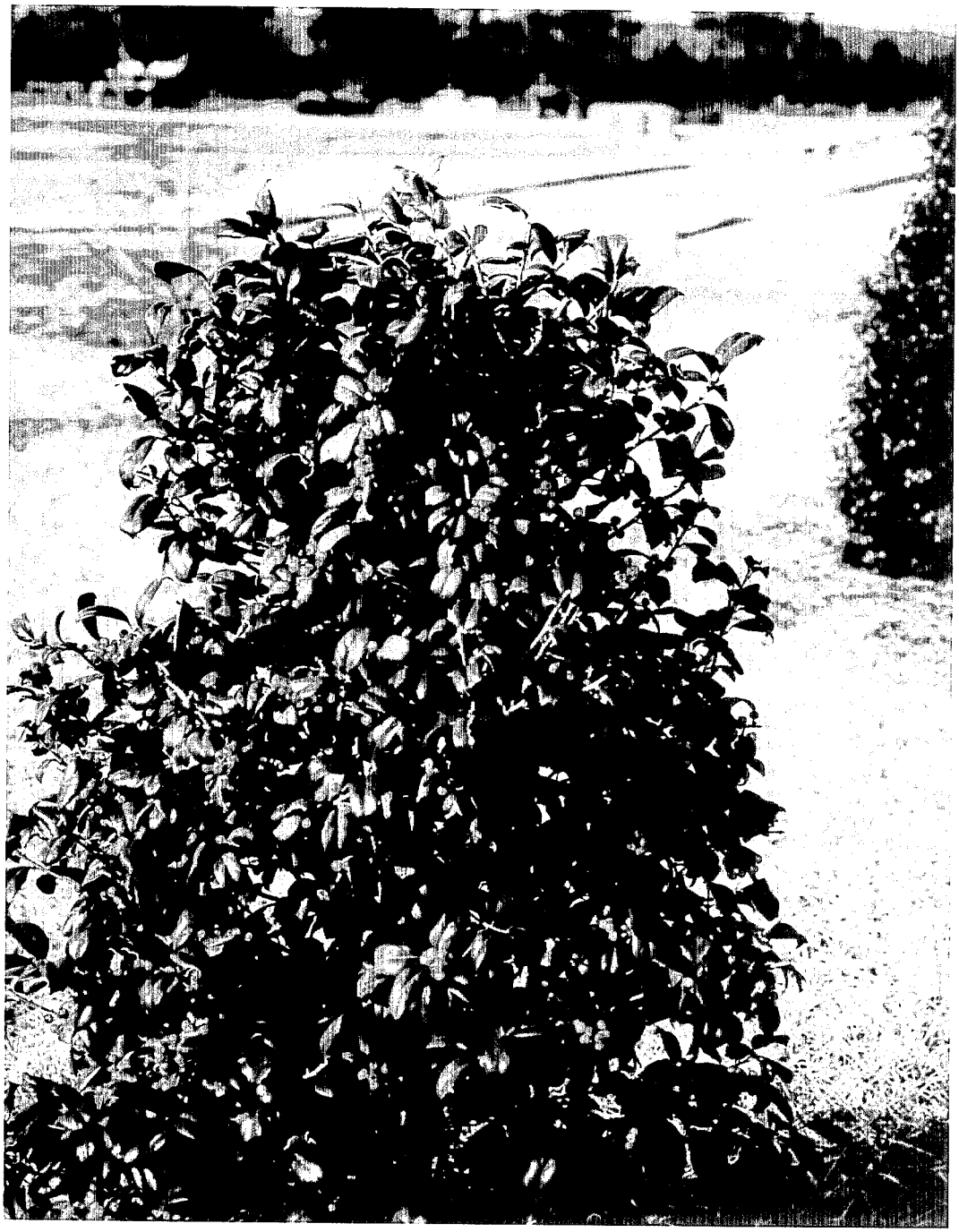
FIG. 1 shows a plant of Ilex ×. 'Wyeriv' as well as the fruit and foliage.
Figure 2:
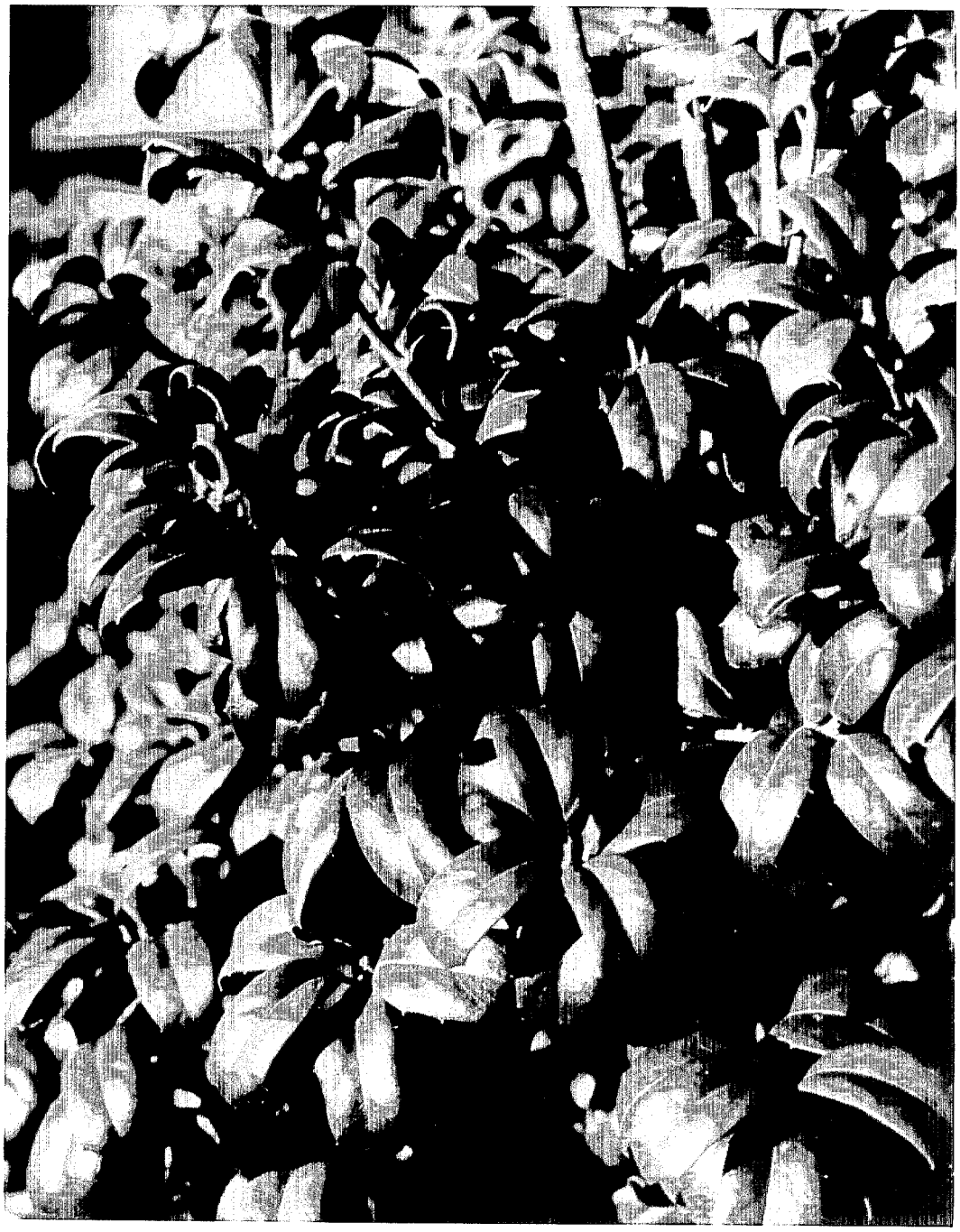
FIG. 2 shows the stem and foliate of Ilex ×. 'Wyeriv'.

Unlike its seed parent, which is pyramidal, mature plants of Ilex ×. 'Wyeriv' are broadly mound shaped. (See FIG. 1) The canopy is dense, even on the inner part of the plant. The canopy of plants of Ilex ×. 'Nellie R. Stevens' that have not been heavily pruned is relatively open. The growth rate of Ilex ×. 'Wyeriv' is less than that of Ilex ×. 'Nellie R. Stevens,' whose terminal buds can produce as much as six feet of growth in one season. A fifteen year old plant Ilex ×. 'Wyeriv' has attained a height of 10 feet and a width of 8 feet. The ultimate height is estimated to be 12–15 feet with a gradual increase in width, which will probably eventually exceed the height.

Berry production for Ilex ×. 'Wyeriv' is comparable with *Ilex cornuta*. Clusters of berries, color group Red 44A, ripening in the second week of October, are distributed over the entire plant. Relatively young plants, 3–4 years old, produce berries. In contrast, Ilex ×. 'Nellie R. Stevens' typically produce a moderate density of berries, color group Red 43A, ripening in early November, and distributed over the entire plant. Berry production does not typically start until the plant is at least six years old.

The leaves are dark green, but not glossy, unlike the leaves of Ilex ×. 'Nellie R. Stevens' which are moderately glossy. The leaves (62–68 mm long; 20–35 mm wide) are slightly smaller than the leaves of Ilex ×. 'Nellie R. Stevens' (75–80 mm long; 43–47 mm wide). The plant is also more winter hardy than its seed parent.

The following qualities of physical appearance and cultural attributes make Ilex ×. 'Wyeriv' unique:

The plant is an appealing evergreen plant, with slightly convex foliage of moderate size, smooth in appearance, and with clusters of attractive red berries in the fall and winter months.

The plant has a moderate growth rate (20–26 cm per year) from primary terminal buds. It produces a growth flush in May and another in September–October in the Mid-Atlantic Region of the United States.

The plant produces abundant quantities of berries that ripen in mid-October, about three weeks before Ilex ×. Nellie R. Stevens, and about two weeks before *Ilex aquipernyi*. The berries are retained on the plant until February or March of the following year. Because of the foliage and berries, cut branches are highly attractive and desirable interior decorations.

The plant has been grown under varied field conditions at Wye nursery for the past 21 years. It has grown well in soils that vary from heavy clay to light sand, but grows best in well drained sandy loam. The plant thrives in both the hot humid summer conditions and the widely fluctuating winter conditions that are characterized of the Eastern Shore of Maryland. Shade tolerance is better than most other cornuta types. It grows best in locations exposed to full sunlight. However, it will tolerate light shade during a portion of the day. The plant holds it color well and has exhibited no noticeable leaf scorching during hot dry summers.

This plant appears to be at least as cold hardy as Ilex ×. Nellie R. Stevens and shows greater hardiness than any of the *Ilex cornuta* types. It has weathered minimum winter temperatures as low as −5° F. to −10° F. with minimal stem damage and no damage to mature (one year or older) growth.

The plant is relatively free of pests or diseases. It has no susceptibility to leaf miners and low attractiveness for mites and scale insects.

DETAILED DESCRIPTION

The following is a detailed description of my new variety of Ilex plant. Color references are in accordance with The Royal Horticultural Society Colour Chart (Royal Horticultural Society, London, England).

Type: Evergreen shrub for use as a foundation or specimen plant in landscaping or for cut boughs to be used as interior decoration. Grows into a broadly mound shaped plant when left unpruned, with multiple stems originating from near the base. (See FIG. 1)

Parentage: Ilex ×. 'Nellie R. Stevens' and a unknown male holly, but showing definite *Ilex cornuta* characteristics.

Localities where grown and observed: Queenstown, Md., and Hilsboro, Md.

Propagation: The distinguishing characteristics are passed on when the plant is propagated by rooted cuttings. The plant is relatively easily propagated by cuttings using conventional techniques for rooting summer or fall hardened growth.

Foliage: The plant is evergreen. The foliage is dark green, but not glossy. Mature leaves are substantially the same color summer and winter. The upper leaf surface is closest to color group 139A. The lower surface is closest to color group 146C. Leaves are slightly convex with one prominent apical spine averaging 2 mm in length, which is always turned downward. There are up to six very small (about 1 mm long) additional spines that are noticeable only on close inspection, irregularly spaced on the leaf margins. Leaves are 20–35 mm wide and 62–68 mm long, typically spaced 22–24 mm apart, on a 9–10 mm petiole. There is no apparent leaf scorch on established plants planted in full sun.

Stems: The current season's growth is uniformly green, closest to color group 146D. Mature bark is closest to color group 199D. Mature bark is 1 mm thick.

Flowers: The flowers are typical of holly. They are pistillate, small (3–4 mm), white, and borne in clusters on the previous season's growth. Blooming time is typical of the genus and varies with the weather and the location. On the Eastern Shore of Maryland the plant typically blooms in late April or early May.

Fruit: The berries are oblate spherical, averaging 7–8 mm through the axis and 10–12 mm in diameter, borne on 8–10 mm penduncles, and produced in clusters. Ripe berries are orange red, closest to color group 44A. (See FIG. 1)

I claim:

1. A new and distinct variety of Ilex plant, substantially as shown and described herein, characterized by its attractive foliage, heavy production of large berries, and adaptability to a wide range of growing conditions.

* * * * *